(12) United States Patent
Liu et al.

(10) Patent No.: US 7,165,463 B2
(45) Date of Patent: Jan. 23, 2007

(54) DETERMINATION OF YOUNG'S MODULUS AND POISSON'S RATIO OF COATINGS FROM INDENTATION DATA

(75) Inventors: Shuangbiao Liu, Peoria, IL (US); Qian Wang, Wilmette, IL (US)

(73) Assignee: Northwestern University, Evanston, IL (US)

(*) Notice: Subject to any disclaimer, the term of this patent is extended or adjusted under 35 U.S.C. 154(b) by 35 days.

(21) Appl. No.: 10/964,589

(22) Filed: Oct. 13, 2004

(65) Prior Publication Data
US 2005/0103120 A1    May 19, 2005

Related U.S. Application Data

(60) Provisional application No. 60/511,487, filed on Oct. 14, 2004.

(51) Int. Cl.
*G01F 1/00* (2006.01)
(52) U.S. Cl. .................................................. 73/861
(58) Field of Classification Search ............. 73/762, 73/763, 788, 790, 794, 795, 799, 761
See application file for complete search history.

(56) References Cited

U.S. PATENT DOCUMENTS

| | | | | |
|---|---|---|---|---|
| 3,763,697 A | * | 10/1973 | Sturm | 73/800 |
| 3,969,928 A | * | 7/1976 | Zarka | 73/785 |
| 4,896,339 A | * | 1/1990 | Fukumoto | 377/19 |
| 5,146,779 A | * | 9/1992 | Sugimoto et al. | 73/81 |
| 5,433,215 A | * | 7/1995 | Athanasiou et al. | 600/587 |
| 6,155,104 A | * | 12/2000 | Suresh et al. | 73/81 |

OTHER PUBLICATIONS

Bhushan, B; Handbook of Micro/nano Tribology, 1999, CRC Press, pp. 270-285.
Fischer-Cripps, Nanoindentation, 2002, Springer, pp. 20-35.
Schneider et al., "Determination of Elastic Modulus and Thickness of Surface Layers by Ultrasonic Surface Waves," Thin Solid Films, vol. 219, n1-2, 1992, pp. 92-102.
Fang, "Determination of the Elastic Modulus of Thin Film Materials Using self-Deformed Micromachined Cantilevers," Journal of Micromechanics and Microengineering, vol. 9, n3, 1999, pp. 230-235.
Loubet et al., "Vickers Indentation Curves of Magnesium Oxide (MgO), " Journal of Tribology, vol. 106, 1984, pp. 43-48.
Doerner et al., "A Method for Interpreting the Data from Depth-Sensing Indentation Instruments," Journal of Materials Research, vol. 1, No. 4, 1986, pp. 601-609.
Pharr et al., "On the Generatlity of the Relationship among Contact Stiffness, Contact Area, and Elastic Modulus During Indentation," Journal of Materials Research, vol. 7, No. 3, 1992, pp. 613-617.
Oliver et al., "An Improved Technique for Determining Hardness and Elastic Modulus Load and Displacement Sensing Indentation Experiments," Journal of Materials Research, vol. 7, No. 6, 1992, pp. 1564-1583.

(Continued)

*Primary Examiner*—Jewel Thompson

(57) ABSTRACT

A method is provided for determining Young's modulus and, if desired, Poisson's ratio of a coating on a substrate wherein load-displacement indentation data in the elastic region (either elastic loading or unloading) generated using an indenter is analyzed to interpret the elastic repsonse of a coated material. The data analysis pursuant to the invention is based on an extended Hertzian analysis developed for thin-film coatings.

17 Claims, 11 Drawing Sheets

OTHER PUBLICATIONS

Chudoba et al., "Step towards a mechanical modeling of layered systems," Surface and Coatings Technology, 154 (2-3), 2002, pp. 140-151.

Gao et al., "Elastic Contact Versus Indentation Modeling of Multi-layered Materials," International Journal of Solids and Structures, 29 (20), 1992, pp. 2471-2492.

Mencik et al., "Determination of Elastic Modulus of Thin Layers Using Nanoindentation," Journal of Materials Research, vol. 12, No. 9, 1997, pp. 2475-2484.

Lim et al., "Accurate Determination of the Mechanical Properties of Thin Aluminum Films Deposited on Sapphire Flats using Nanoindentations, " Journal of Materials Research, vol. 14 (6), 1999, pp. 2314-2326.

Wallace et al., "Elastic Modulus Measurements in Plasma Sprayed Deposits," Journal of Thermal Spray Technology, vol. 7 (4), 1998 pp. 521-526.

Herbert et al., "On the Measurement of Stress-strain Curves by Spherical Indentation," Thin Solid Films, vol. 398-399, 2001, pp. 331-335.

Chudoba et al., "Determination of elastic properties of thin films by indentation measurements with a spherical indenter," Surface and Coatings Technology, 127(1), 2000, pp. 9-17.

Nogi and Kato, T., "Influence of a Hard Surface Layer on the Limit of Elastic Contact-Part II: Analysis Using a Real Surface Model," ASME Journal of Tribology, vol. 119, 1997, pp. 493-500.

Liu and Wang, "Studying Contact Stress Fields Caused by Surface Tractions with a Discrete Convulution and Fast Fourier Transform Algorithm," Journal of Tribology, vol. 124, 2002, pp. 36-45.

Liu and Wang, "A Three-dimensional Thermomechanical Model of Contact Between Non-Conforming Rough Surfaces," Journal of Tribology, vol. 123, 2001, pp. 17-26.

Schneider et al., "Non-destructive Characterization and Evaluation of Thin Films by Laser-induced Ultrasonic Surface Waves," Thin Solid Films, 290-291, 1996, pp. 305-311.

Johnson, Contact Mechanics, Cambridge University Press, 1985, pp. 84-103.

Schwarzer et al., "The elastic field in a coated half-space under Hertzian pressure distribution," Surface and Coating Technology, 114, 1999, pp. 292-304.

* cited by examiner

DETERMINATION OF YOUNG'S MODULUS AND POISSON'S RATIO OF COATINGS FROM INDENTATION DATA

This application claims benefits and priority of U.S. provisional application Ser. No. 60/511,487 filed Oct. 14, 2004, the entire disclosure of which is incorporated herein by reference.

CONTRACTUAL ORIGIN OF THE INVENTION

Funding of the invention was provided in part by the Office of Naval Research under Grant No. N00014-01-1-0392/P00001. The Government may have certain rights in the invention.

FIELD OF THE INVENTION

This invention relates to a method of determining Young's modulus for coatings with uniform coating thickness and, more particular, to a method of determining Young's modulus and optionally Poisson's ratio for thin-film coatings using load-displacement indentation data in the elastic range in an efficient, accurate and non-destructive manner.

BACKGROUND OF THE INVENTION

Young's modulus, or elastic modulus (E), and Poisson's ratio (v) are two of the key mechanical properties of materials. Modern thin-film technologies have provided means for the development of coatings for various applications in mechanical, electrical, and biomedical engineering to protect the surfaces of components that bear load and transmit motion for performance and life enhancement. Such coating development demands an efficient and reliable, yet convenient, technology for the determination of the Young's modulus and Poisson's ratio of the coatings.

Currently, five techniques are commonly used for the measurements of the Young's modulus of thin-film coatings: (1) indentation, (2) beam bending, (3) vibration, (4) ultrasonic surface wave, and (5) scanning acoustic microscope (References: Bhushan 1999, Fischer-Cripps 2002, Schneider et al. 1992, and Fang 1999). Among these methods, indentation is the most popular technique, with which Young's modulus is often determined through the initial part of the unloading curve of an indentation data with sharp-pointed indenters (References: Loubet et al. 1984, Doerner and Nix 1986, Pharr et al. 1992, and Oliver and Pharr 1992). However, determining Young's modulus of a coating through this technique, at the macro, micro, or nano scale, has the following drawbacks. (1) The indentation data are indispensably contaminated by the response of the substrate materials under the coating to be measured. In order to minimize the substrate influence on properties measurement, the maximum indentation displacement (i.e. mutual approach or depth) is empirically limited to one-tenth of the coating thickness. This empirical requirement is not suitable for modulus measurement (References: Chudoba et al. 2002). Empirical and theoretical expressions have been proposed to account for the substrate influence on the measurement, e.g. References: Doerner and Nix 1986, Gao et al. 1992, and Menčík et al. 1997. (2) The indenters have to be made sharp in order to have meaningful coating response under such shallow indenter penetration. The tip shape often deviates from the ideal one (rounded) and the indenters are easily damaged. (3) The indentation process is destructive. Dents are left in the sample after examination. In the neighborhood of dents, materials undergo the work-hardening process due to plasticity. For ceramic coatings, coating cracking usually accompanies the indentation process and affects the result of measurement. (4) For polymers, creeping may occur in the loading-unloading process and affect the result of measurement. (5) Existing models cannot accurately determine the contact area. For example, material pileup is significant in the indentation of thin-film and affected by the residual stress in the sample. The material pileup and plastic deformation under the indenter also change the coating thickness on the measurement site. (References: Lim et al. 1999). (6) Measured modulus is a modified Young's modulus, which equals Young's modulus divided by the difference between unity and square of Poisson's ratio.

Indentation displacement and force could be measured very accurately. For example, a commercial nanoindentation system could achieve the displacement resolution of 0.1 nm and the force resolution of 1 μN. The data analysis of recorded load-displacement indentation data is critical to the testing goal, such as determination of Young's modulus. Traditional indentation is in elastic-plastic range and Young's modulus is determined by elastic punch models (References: Loubet et al. 1984, Doerner and Nix 1986, Pharr et al. 1992, Gao et al. 1992, and Oliver and Pharr 1992) with the projected contact area and the slope of the load-displacement curve at the beginning of the unloading. Poisson's ratio for the sample is not determined but estimated. References (e.g., Wallace and Ilavsky 1998; Herbert et al. 2001) showed that Hertzian theory could be applied to determine the modified Young's modulus of a homogeneous sample by a spherical indenter in the elastic range. For thin-film coatings, References: Chudoba, Schwarzer and Richter (2000) showed the possibility to determine the modified Young's modulus by a spherical indenter working in the elastic range. An analytical solution for the indentation displacement due to an estimated (inaccurate) Hertzian pressure distribution is utilized to calculate the modified Young's modulus of a thin-film through a curve-fitting process of the load-displacement curve obtained from a depth-sensing measurement. However, the assumed Hertzian pressure distribution is not the true contact pressure between the spherical indenter and the coated sample, and because of the lack of the relationship between displacement and load a curve-fitting process has to be used. In all known indentation data analysis, Poisson's ratio is always assumed a priori.

SUMMARY OF THE INVENTION

The present invention provides a method for determining the Young's modulus and, if desired, Poisson's ratio of a coating on a substrate wherein load-displacement indentation data generated in the elastic region (either elastic loading or unloading) is analyzed to interpret the elastic response of the coated substrate. The data analysis is based on an extended Hertzian analysis developed for thin-film coatings pursuant to the invention.

In one embodiment of the present invention, a method of the invention involves the steps of generating load versus displacement indentation data using an indenter to indent a coated sample having a coating on a substrate in an elastic range of the coating; determining a modified Young's modulus of the coated sample ($E^*_s$) using the indentation data; and determining the Young's modulus of the coating ($E_c$) using a relationship that expresses the modified Young's modulus of the coated sample ($E^*_s$) as a function of the Young's modulus and Poisson's ratio of the coating, the Young's modulus and Poisson's ratio of the substrate, and a parameter related to thickness of the coating. In a particular embodiment, the relationship is expressed as:

$$E_s^* = E_c^* \frac{1 - (\lambda + \kappa + 4\kappa\alpha^2)\theta + \lambda\kappa\theta^2}{1 + 4\alpha\kappa\theta - \lambda\kappa\theta^2}$$

where $$\tau = \frac{E_c(1 + v_b)}{E_b(1 + v_c)}$$

is the shear modulus ratio;

$$\kappa = \frac{\tau - 1}{\tau + (3 - 4v_c)} \text{ and } \lambda = 1 - \frac{4(1 - v_c)}{1 + \tau(3 - 4v_c)},$$

and $\theta = \exp(-2\alpha)$ where parameter $\alpha$ is related to non-dimensional coating thickness.

The invention further can be practiced to determine the Young's modulus and Poisson's ratio of the substrate using this relationship.

In practicing embodiments of the invention, the indenter can include an uncoated surface that indents the sample or a coated surface that indents the sample.

The present invention is useful to accurately, conveniently and non-destructively determine Young's modulus and Poisson's ratio of a coating (including thin-film coating) concurrently through indentation testing. The method can be used as a stand-alone analysis method or can be incorporated into and practiced in conjunction with existing nanoindentation systems.

The present invention is advantageous as follows:

(1) During the indentation measurement, curve fitting is eliminated.
(2) The indentation measurement is conducted in the elastic range of loading and therefore is non-destructive. No crack, material pileup, or dent of the coating occurs.
(3) No plasticity is involved, so that the Young's modulus is not disturbed by residual stress or the possible work hardening effect.
(4) A preferred method embodiment practiced with spherical indenters does not require the estimation of contact area, which usually involves large error.
(5) The indenter is a spherical ball or other body with a spherical tip, easy to make and can be repeatedly used. Furthermore, any hard materials with or without a coating can be used to make the indenter ball. Therefore, the indenter cost is reduced.
(6) The method works for testing any coating, which can be hard or soft, and comprise metallic, ceramic, or organic materials, and any substrate material.

These and other advantages of the present invention will become more readily apparent from the following detailed description taken with the following drawings.

DESCRIPTION OF THE DRAWINGS

In FIG. 1a, the coating with thickness $t_c$ is deposited on the fixed base and the total thickness of sample is $t_t$. The coating has mechanical properties; Young's modulus $E_c$ and Poisson's ratio $v_c$, while the base or substrate has Young's modulus $E_b$ and Poisson's ratio $V_b$. The indenter has a radius of R and its mechanical properties are $E_i$ and $v_i$. Before load is applied, the indenter and the sample touch each other but there is no indentation displacement (the dotted lines). After load P is applied, both the indenter and the sample are deformed (the deformation of the indenter is not shown in all figures). The contact radius is denoted by a and the indentation displacement is denoted by h. The indentation displacement is the traveling distance of a material point in the indenter far way from the contact interface, e.g. the center of the sphere. The load and the displacement are recorded at specific steps when the load is increased.

DETAILED DESCRIPTION OF THE INVENTION

The present invention provides a method for determining the young's modulus and, if desired, Poisson's ratio of a coating on a substrate (providing a coated sample) as well as of the substrate wherein load-displacement indentation data in the elastic region (either elastic loading or unloading) generated using an indenter is analyzed to interpret the elastic response of the coated sample. The data analysis pursuant to the invention is based on an extended Hertzian theory developed pursuant to an embodiment of the invention for thin-film coatings.

As background, the classic Hertzian theory presents exact contact solutions for contact pressure, displacement, and contact area between two elastic, isotropic, frictionless solids in contact and has been widely applied in engineering practice, including measurements of the modified Young's modulus through depth-sensing techniques, e.g. References: Wallace and Ilavsky (1998). The formula used for determination of the modified Young's modulus is the relationship between load and displacement derived by Hertz (1882), $$E_{is} = \frac{3P}{4\sqrt{R^* h^3}} \quad (1)$$

where h is the displacement and P is the load applied on the indenter with a radius R. $E_{i\,s}$ is the reduced Young's modulus of the indenter and the sample, $$\frac{1}{E_{is}} = \frac{1}{E_i^*} + \frac{1}{E_s^*} \quad (2)$$

Subscripts i and s indicate the indenter and the sample, respectively. E with a superscript '*' denotes the modified Young's modulus of homogeneous materials, $$E^* = \frac{E}{1 - v^2} \quad (3)$$

R* in Eq. (1) is the modified radius. With known R* and $E^*_i$, a data point on the load-displacement curve gives a $E^*_s$ value from Eqs. (1) and (2). The sample is generally assumed to be nominally flat. If the sample is free of plastic deformation, R* simply equals R, the radius of the indenter. Otherwise the radius, $R_r$, of the impression due to plastic deformation will contribute to R*, $$\frac{1}{R^*} = \frac{1}{R} - \frac{1}{R_r} \quad (4)$$

$R_r$ could be measured from imaging techniques. The mechanical properties and the radius of the indenter are often given beforehand or could be calibrated as described hereafter. With the load-displacement curve, one can determine $E_{i\,s}$ from Eq. (1) and $E^*_s$ from Eq. (2). By assuming a proper Poisson's ratio of the sample, the Young's modulus of a homogeneous sample can be determined.

However, for coated bodies, the classic Hertzian theory is not applicable to determine mechanical properties of the coating.

Figure 1A:
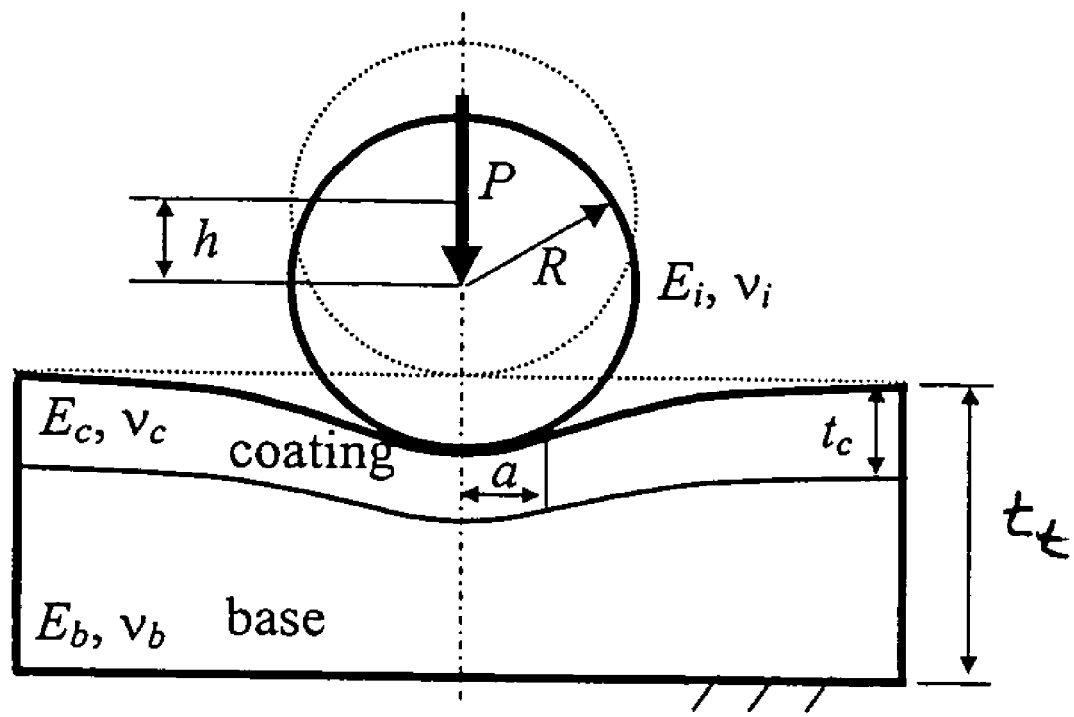
FIG. 1a shows schematically the indentation testing of a coated sample with a flat surface for measuring of the Young's modulus and Poisson's ratio of the coated sample. The coated sample comprises a coating on a base or substrate as shown.
Figure 1B:
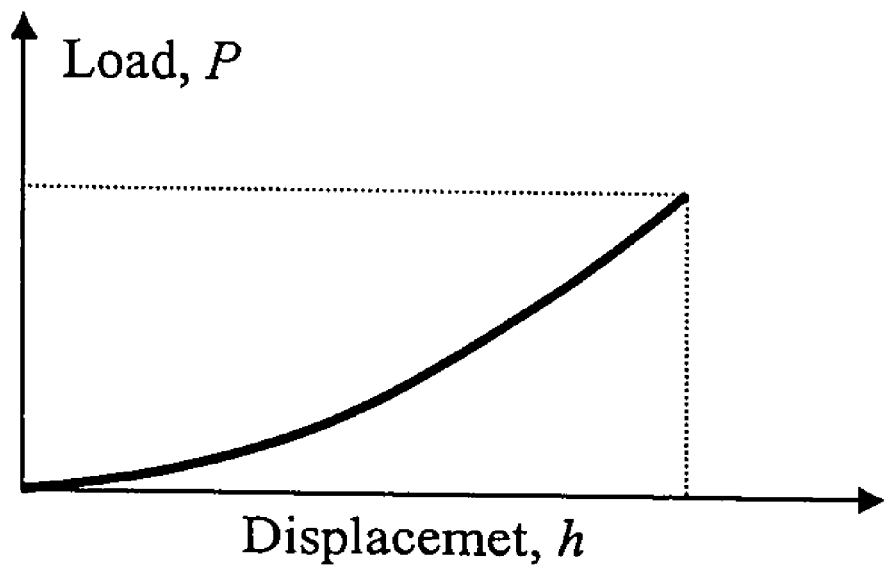
FIG. 1b is a schematic load (P) versus displacement (h) curve generated by the above described indentation test.

The present invention involves extending or modifying the classic Hertzian analysis to enable determination of mechanical properties (i.e. Young's modulus and Poisson's ratio) of coated substrates or bodies (coated samples) illustrated in FIG. 1. For example, the coated sample is illustrated including two different parts: a substrate (base) and a thin-film coating, which are bonded perfectly to each other. Their mechanical properties (i.e. Young's modulus E and Poisson's ratio v) are labeled by subscripts b and c for the base (substrate) or the coating, respectively. The contact consequence of the indenter and the sample should be between two limiting cases: the contact of the indenter and the sample with (a) zero and (b) infinity coating thickness. Both limiting cases can be predicted by the Hertzian analysis. The contact radius in the first limiting case (with zero coating thickness) is denoted by $a_0$, which can be calculated by the Hertzian analysis, $$a_0 = \sqrt[3]{\frac{3PR}{4E_{ib}}} \quad (5)$$

where $E_{i\,b}$ is the reduced Young's modulus, consisting of the modified modulus of the indenter and the base material, $$\frac{1}{E_{ib}} = \frac{1}{E_i^*} + \frac{1}{E_b^*} \quad (6)$$

Quantity $a_0$ is used to normalize coating thickness, $t_c$. The dimensionless coating thickness is expressed as $$T_c = t_c/a_0 \quad (7)$$

For the contact between the indenter and coated body (coated sample), it is found that one can adopt the forms of Eqs. (1) and (2) originally presented by the classic Hertzian anaylsis, but redefine $E^*_s$ in Eq. (2). Thus $$Eq.\ (1){:}\ E_{is} = \frac{3P}{4\sqrt{R^* h^3}}$$

$$Eq.\ (2){:}\ \frac{1}{E_{is}} = \frac{1}{E_i^*} + \frac{1}{E_s^*}$$

-continued $$E_s^* = E_c^* \frac{1 - (\lambda + \kappa + 4\kappa\alpha^2)\theta + \lambda\kappa\theta^2}{1 + 4\alpha\kappa\theta - \lambda\kappa\theta^2} \quad (8)$$

where $$\tau = \frac{E_c(1 + v_b)}{E_b(1 + v_c)}$$

is the shear modulus ratio;

$$\kappa = \frac{\tau - 1}{\tau + (3 - 4v_c)} \text{ and } \lambda = 1 - \frac{4(1 - v_c)}{1 + \tau(3 - 4v_c)}$$

are similar to the Dundurs parameters (see References: Johnson, K. L. 1985); and $\theta = \exp(-2\alpha)$. Here, Equation (8) is derived by comparing the normal deformation expression for a layered medium in the frequency domain (see Nogi and Kato, T., 1997 "Influence of a Hard Surface Layer on the Limit of Elastic Contact-Part 1: Analysis Using a Real Surface Model", ASME Journal of Tribology, 119, pp. 493–500) with that for a homogenous medium (the same expression, but with the film thickness being zero). Parameter $\alpha$ is related to the non-dimensional coating thickness, $T_c$.

Note that $E^*_s$ is now a function of coating thickness and material properties of the coating and the substrate. The essence of Eq. (8) is that the coated sample is equivalent to a homogenous virtual sample with a modified modulus depending on the dimensionless coating thickness. When $\alpha$ is infinity (no substrate at all and $\theta$ is zero), it is evident that $E^*_s$ in Eq. (8) equals $E^*_c$. In this case, the sample is solely composed of the coating material. On the other hand, it can be verified that when $\alpha$ is zero, the fraction in Eq. (8) can be simplified as, $$\frac{1 - (\lambda + \kappa) + \lambda\kappa}{1 - \lambda\kappa} = \frac{E_b^*}{E_c^*} \quad (9)$$

which equals $1/E_{mr}$, where $E_{mr} = E^*_c/E^*_b$ is defined as the coating-to-base modulus ratio. Thus, in the case of zero $\alpha$ (no coating at all), one can find $E^*_s$ in Eq. (8) equals $E^*_b$ with the help of Eq. (9). Indeed, these two special cases are the two limiting cases mentioned above. Equation (8) together with Eqs. (1) and (2) pursuant to the invention extend the Hertzian analysis to solve indentation problems with coated samples.

The parameter $\alpha$ appearing in $\theta$ and Eq. (8) is determined beforehand with numerical simulations described hereafter. The extended Hertzian analysis consists of Eqs. (1), (2) and (8) and suitable $\alpha$. In the following, a procedure with numerical simulations is presented to determine $\alpha$ beforehand. Since numerical simulations need specific conditions, an arbitrary set of parameters is chosen in the beginning. However, it is shown in the end of the procedure that the results of $\alpha$ work well for a wide range of conditions. The flat base (substrate) is assumed to be made of steel and has Poisson's ratio ($v_b$) of 0.3 and Young's modulus ($E_b$) of 200 GPa. The indenter has radius (R) of 12 mm and is assumed to be rigid. Note that in the literature, rigid indenter assumption is widely used for derivation purpose. A load (P) of 400 N is applied on the indenter. These parameters determine $a_0$, ≈0.254 um. The dimensionless thickness of the coating ($T_c$) varies from 0.01 to 3. Poisson's ratio ($v_c$) of the coating is set as 0.3 and $E_{mr}$ ($E_{mr} = E^*_c/E^*_b$) varies from 0.25 to 4.

The corresponding displacement h for the combination of conditions selected in the preceding paragraph is evaluated using a numerical code or analysis of the type developed by Liu and Wang in "Studying Contact Stress Fields Caused by Surface Tractions with a Discrete Convolution and Fast Fourier Transform Algorithm", Journal of Tribology, Vol. 124, pp. 36–45 2002, and in "A Three-Dimensional Thermomechanical Model of Contact Between Non-Conforming Rough Surfaces", Journal of Tribology, Vol. 123, pp. 17–26 2001, the teachings of both of which are incorporated herein by reference. The numerical analysis involves an iteration process to modify pressure distribution (initial value is simply external load divided by simulation area) between two bodies in contact so that contact conditions could be fulfilled. These conditions are: a) the external load should be balanced by interfacial force due to the resolved pressure, b) when two surfaces of the bodies in contact are separate, pressure should be zero; otherwise c) pressure should be greater or equal to zero. The input parameters are external load, geometry and material properties of each body, and coating thickness. The numerical analysis determines contact pressure, displacement h, gap between two surfaces, among other outputs.

Figure 2:
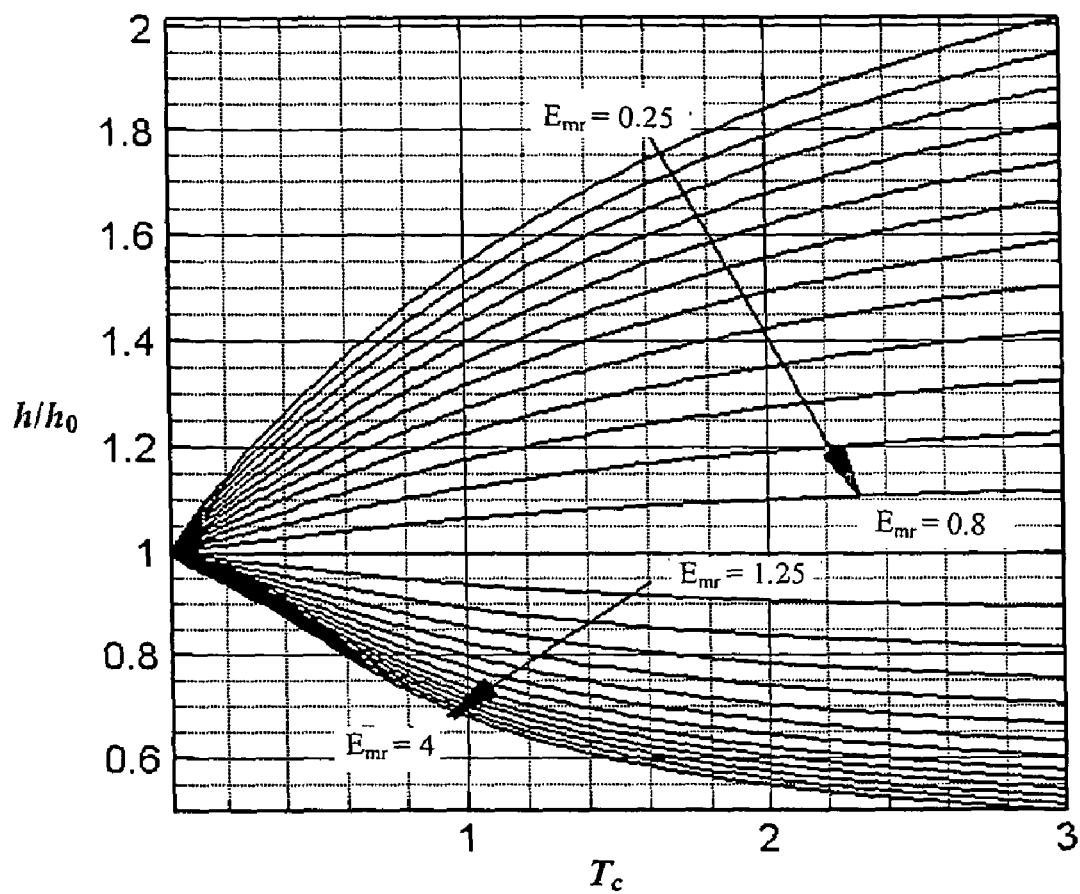
FIG. 2 shows numerical results of normalized displacement ($h/h_0$) versus normalized coating thickness ($T_c$) with different modulus ratios ($E_{mr}$).

FIG. 2 shows the displacement values obtained for the above-described combination of conditions, the displacment h being normalized by $h_0$, which is the displacement under the same conditions except zero $T_c$. If $T_c$ is large enough, it is expected that each curve in FIG. 2 should reach a certain value. It is apparent that the substrate effect is significant even when the coating thickness is three times of $a_0$. Similar to Eq. (1), one can write $$E_{ib} = \frac{3P}{4\sqrt{R^*h_0^3}}.$$

Therefore, the normalized displacement can be written as $$\frac{h}{h_0} = \left(\frac{E_{ib}}{E_{is}}\right)^{2/3} = \left[\frac{E_b^*(E_s^* + E_i^*)}{E_s^*(E_b^* + E_i^*)}\right]^{2/3}$$

Since the indenter is rigid, substitution of $E^*_s$ in Eq. (8) into the above equation gives $$\frac{h}{h_0} = \left(\frac{E_b^*}{E_s^*}\right)^{2/3} = \left\{\frac{1 + 4\alpha\kappa\theta - \lambda\kappa\theta^2}{E_{mr}[1 - (\lambda + \kappa + 4\kappa\alpha^2)\theta + \lambda\kappa\theta^2]}\right\}^{2/3} \quad (10)$$

Figure 3:
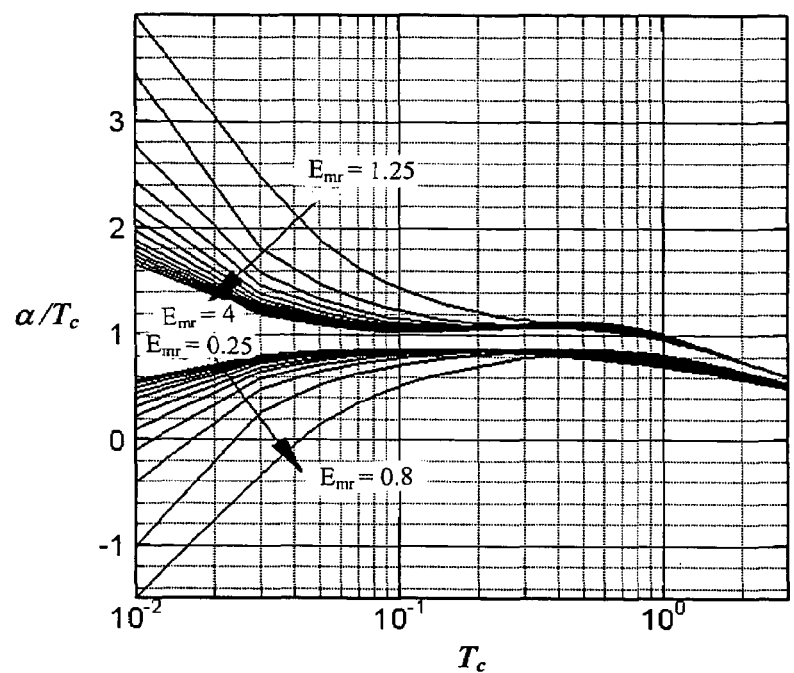
FIG. 3 shows parameter $\alpha$ for all conditions investigated in the numerical analyses (FIG. 2). Parameter $\alpha$ is determined by using displacement data in FIG. 2 and Eq. (Equation) (10).
Figure 4:
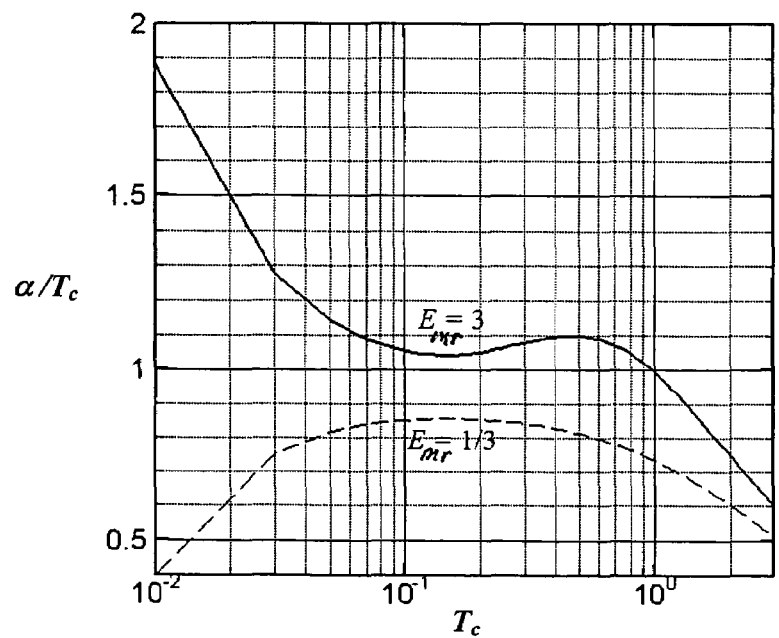
FIG. 4 shows the representative $\alpha$, which is a function of dimensionless coating thickness, for all ratios of Young's modulus shown.

For different $E_{mr}$ and coating thickness, Eq. (10) and displacement curves in FIG. 2 are used to determine $\alpha$ so that Eq. (10) with these $\alpha$ values gives almost identical displacement to FIG. 2. FIG. 3 depicts the results of $\alpha/T_c$ against $T_c$ with different coating/base modulus ratios $E_{mr}$. It is noted that in the range of small $T_c$, value of $\alpha/T_c$ is strongly dependent on the ratio of $E_{mr}$. Curves with $E_{mr}$ greater than one are above those with $E_{mr}$ less than one. Curves with two extreme $E_{mr}$ values (0.25 and 4) are close to unity. Some negative values are obtained for $\alpha$ when $E_{mr}<1$. It is of interest to find representative $\alpha$ which could be a function of coating thickness, but should be independent of the ratio $E_{mr}$. If this kind of a rather than those exact values depicted in FIG. 3 is used to predict displacement with Eq. (10), discrepancy between the predicted displacement and that in FIG. 2 is expected to occur and should be acceptably small. FIG. 4 presents such two sets of a which are picked out from FIG. 3 with $E_{mr}=3$. Error used to quantify the discrepancy is defined as the difference in percentage between the values predicted with Eq. (10) and the values in FIG. 2 (numerical solutions) normalized by the latter. The relative error shown in FIG. 5 demonstrates the discrepancy between predicted and numerical ones is within one percent for $E_{mr}>1$ and within two percent for $E_{mr}<1$. In order to facilitate data processing, curves in FIG. 4 are replaced by the following simple expressions, $$\frac{\alpha}{T_c} = \begin{cases} 1.065, & T_c < 0.25 \\ 0.948 + 0.637 T_c - 0.683 T_c^2, & 0.25 \le T_c < 0.5 \\ 1.064 + 0.211 T_c - 0.287 T_c^2, & 0.5 \le T_c < 0.9 \\ 1.328 - 0.382 T_c + 0.0466 T_c^2, & 0.9 \le T_c \end{cases} \quad (11)$$

Figure 5:
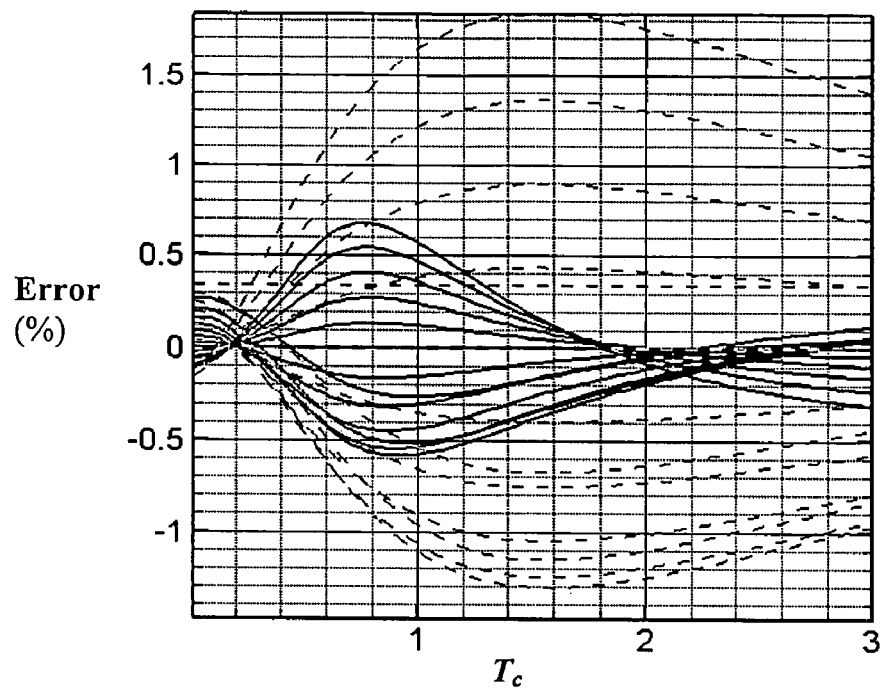
FIG. 5 shows the relative error of predicted displacement using the extended Hertizian theory in percentage and the $\alpha$ values of FIG. 4 where solid lines are $E_{mr}$ greater than 1 and dashed lines are $E_{mr}$ less than 1. In order to verify that data in FIG. 4 works for other modulus ratios $E_{mr}$, Eq. (10) is used to predict the displacement. The relative error is defined as the difference between predicted and numerical results divided by numerical results.

The corresponding relative error with this function of $\alpha$ is similar to what is depicted in FIG. 5. As mentioned before, the validity of Eq. (11) should be tested for changing the following conditions: Poisson's ratio of coating, load, indenter's radius, and Young's modulus of the indenter. Several such tests have been carried out. It is found that the change of load and indenter's radius has no effect on the relative error and the change of Poisson's ratio and Young's modulus of the indenter slightly affects the relative error. Therefore, the extended Hertzian analysis and Eq. (11) pursuant to an embodiment of the invention reflect the relationship between load and displacement to a satisfactory degree.

Figure 6:
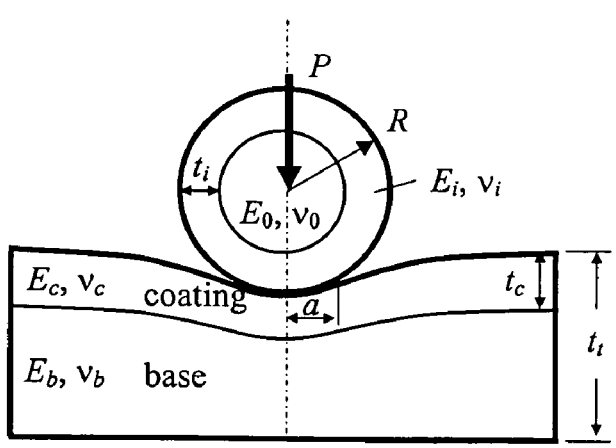
FIG. 6 shows the configuration of a coated indenter in the indentation testing. The base of the indenter has mechanical properties $E_0$ and $v_0$, and the coating perfectly bonded on it has $E_i$ and $v_i$. The coating of the indenter has a thickness of $t_i$. Other parameters are the same as in FIG. 1.

The fraction on the right-hand side of Eq. (8) is corresponding to the presence of the substrate. Note that the Young's modulus expression of the sample includes the Young's moduli and the Poisson's ratios of the coating and the substrate and $\alpha$ which is related to coating thickness. Similarly, if the indenter is covered by a coating (FIG. 6), $E^*_i$ in Eq. (2) should be expressed in the same way as $E^*_s$. Therefore, coated indenters could be used to probe the sample's modulus.

Figure 13:
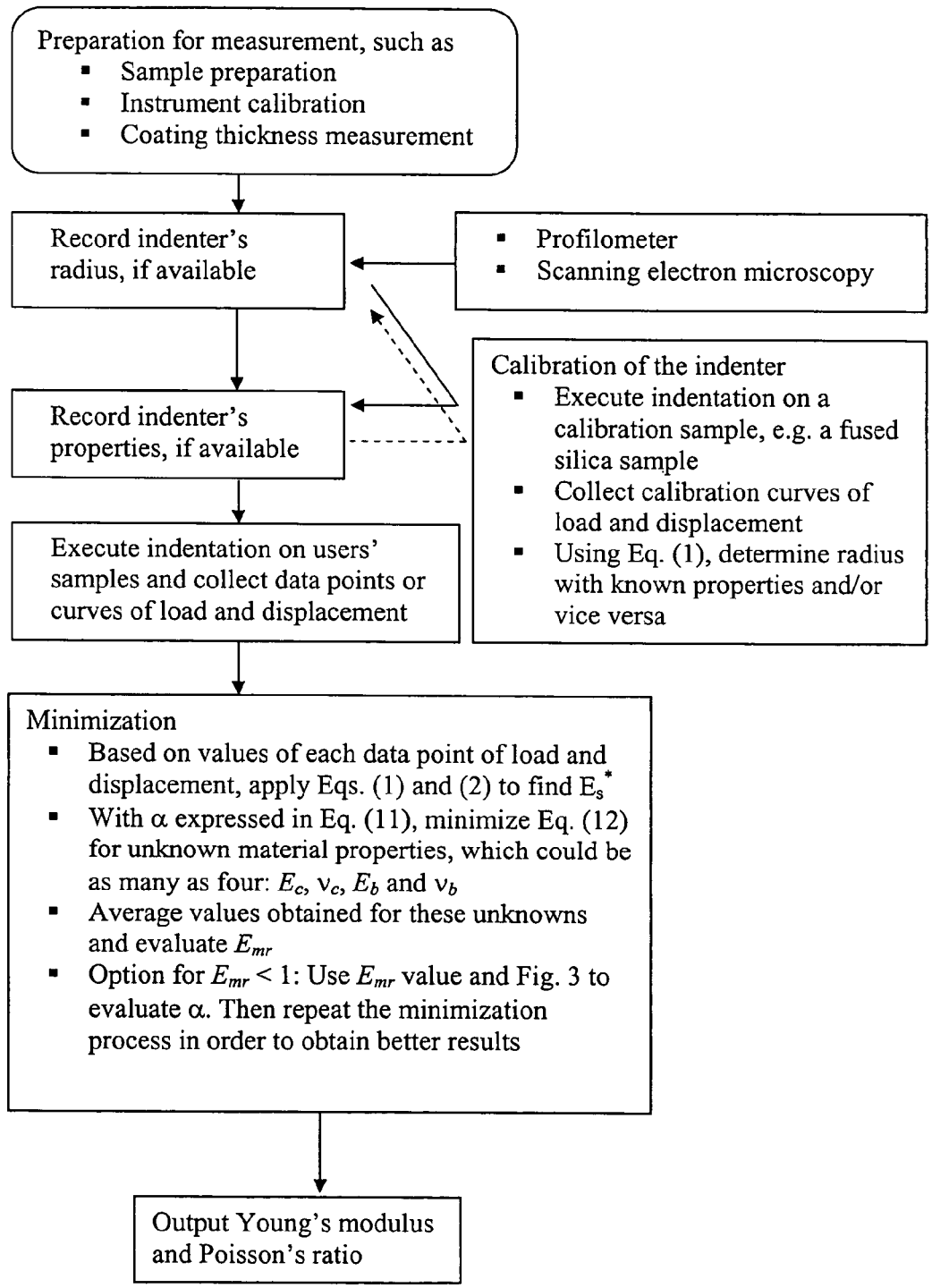
FIG. 13 is a flow chart illustrating a method aspect of the present invention.

A method to determine Young's modulus and Poisson's ratio of the coating and the substrate pursuant to an embodiment of the invention is described as follows and illustrated in FIG. 13:

1. The sample is prepared and the indenter instrument properly calibrated.
2. The coating thickness of the sample is known or measured with proper methods. Choose a spherical indenter with a radius much greater than the coating thickness. The indenter could be made of diamond, sapphire, ruby, tungsten carbide, or other materials.
3. Record the modified Young's modulus and radius of the indenter, if these data are available.
4. If the radius of the indenter is not available, one could use instruments, such as profilometer or scanning electron microscopy, to determine it.
5. If necessary, a calibration sample with known material properties, e.g. fused silica, can be used to calibrate the modified Young's moduli or the radius of the indenter. After the calibration sample is indented by the indenter, the load-displacement curve is obtained. In the calibration with known indenter's radius, Eq. (1) is used to find $E_{i,s}$, which is then used to determine $E^*_i$ from Eq. (2). In the calibration with known modified Young's moduli of the indenter, Eq. (2) is used to find $E_{i,s}$, which is then used to determine R from Eq. (1) and Eq. (4).
6. Estimate the maximum load and make sure the load is applied within the elastic range. Record one or several data sets of the load and the displacement.
7. $T_c$ is evaluated by Eqs. (5) and (7) with load values corresponding to measured data points.
8. Use Eq. (1) to obtain $E_{i,s}$ with load and displacement values corresponding to measured data points.
9. Use Eq. (2) to find $E^*_s$.
10. Equation (8) is used to find Young's modulus of the coating $E_c$ and Poisson's ratio of the coating $v_c$, and to find similar properties of the base $E_b$ and $V_b$ as well if they are unknown. Conventional minimization analysis can be used to find values of these properties by minimizing (i.e minimizing error) the following expression rewritten from Eq. (8), $$\left| E^*_s - E^*_c \frac{1 - (\lambda + \kappa + 4\kappa\alpha^2)\theta + \lambda\kappa\theta^2}{1 + 4\alpha\kappa\theta - \lambda\kappa\theta^2} \right| \quad (12)$$

where $\alpha$ values are expressed in Eq. (11).
11. Average Young's modulus and Poisson's ratio values obtained in step 10 and evaluate $E_{mr}$.
12. In order to improve the accuracy, particularly for $E_{mr}<1$, the $E_{mr}$ value is used to determine $\alpha$ value from FIG. 3 by interpolation.
13. Repeat steps 10 and 11.

EXPERIMENTAL EXAMPLES

Figure 7A:
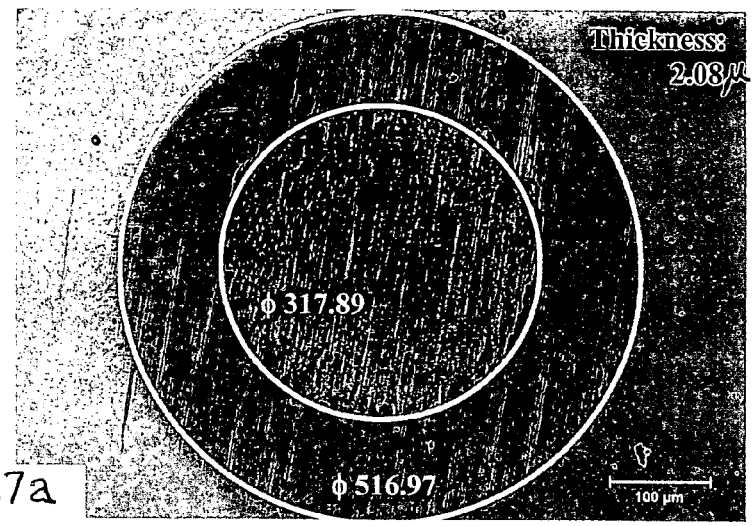
FIGS. 7a and 7b show the conventional measurements of wear scars for coated samples A1 and A2 in order to determine coating thickness.
Figure 7C:
FIG. 7c shows schematically a ball with radius of 10 mm that is used to remove each coating. After measuring the diameters of the corresponding circles, one can determine the coating thickness; e.g. sample A1 and A2 have a respective coating thickness of 2.08 and 3.15 microns.
Figure 7B:
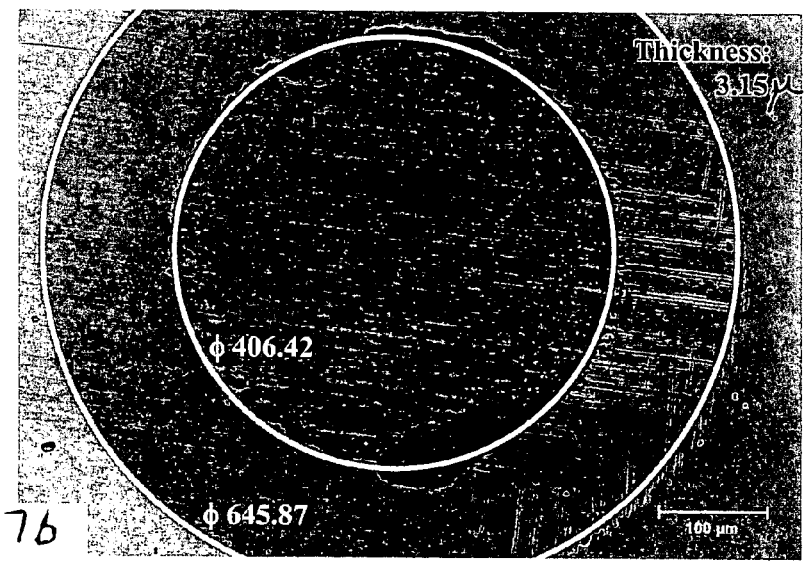
Figure 8:
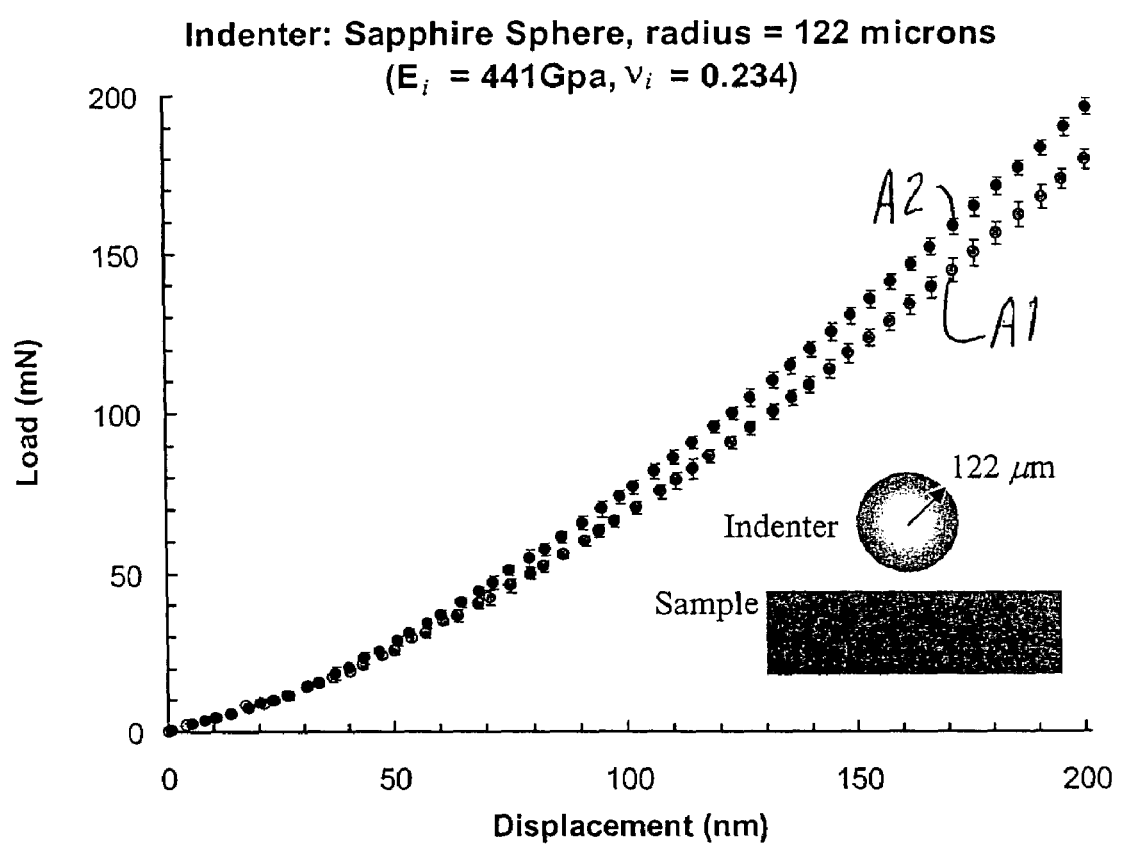
FIG. 8 shows indentation data of load vs displacement for each of coated samples A1 and A2 from nine measurements using a sapphire indenter ball of 122 microns radius and $E_i$ of 441 GPa and $v_i$ of 0.234 as shown. The data is the average of the nine tests in the loading portion with a displacement less than 200 nm. Error bars show the standard deviation of the nine tests.
Figure 9:
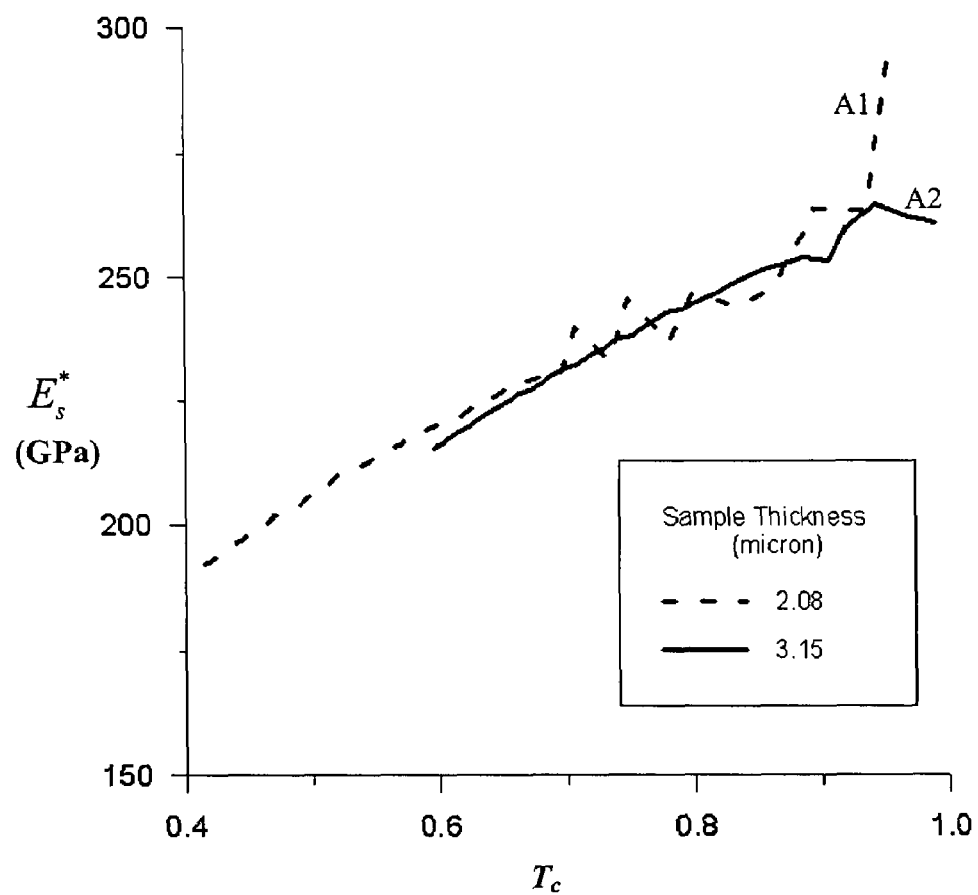
FIG. 9 shows the relation between modified Young's modulus of coated samples A1 and A2 and normalized coating thickness ($T_c$) obtained from average indentation data shown in FIG. 8. Results for $T_c$ greater than 1, which are corresponding to measurements with small displacement, are not shown.
Figure 10A:
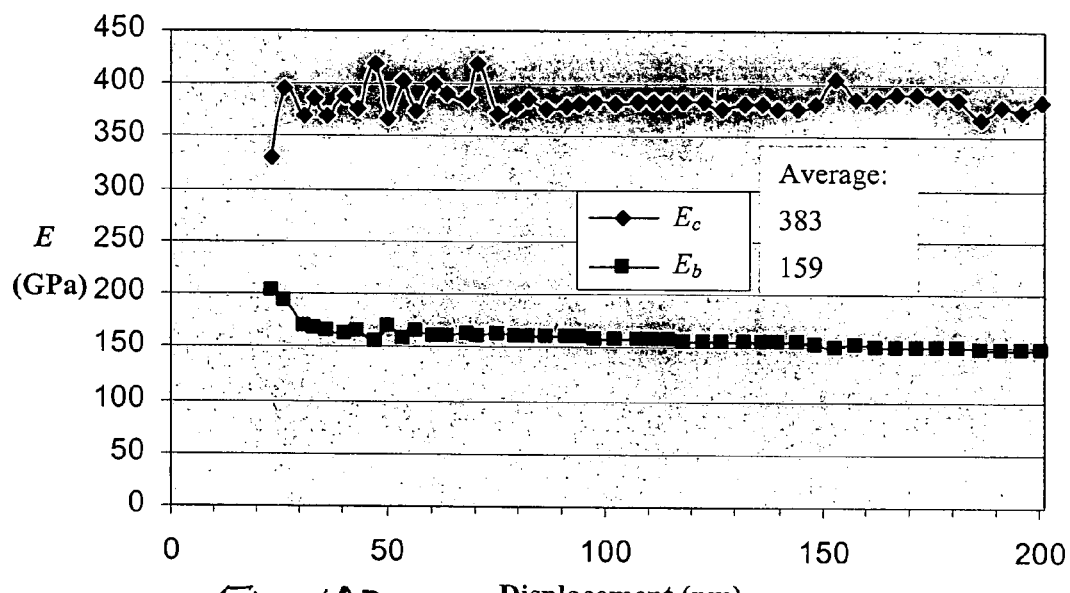
FIGS. 10a and 10b show predicted Young's modulus values and Poisson ratio values, respectively, for sample A1 for each discrete indentation measurement.
Figure 10B:
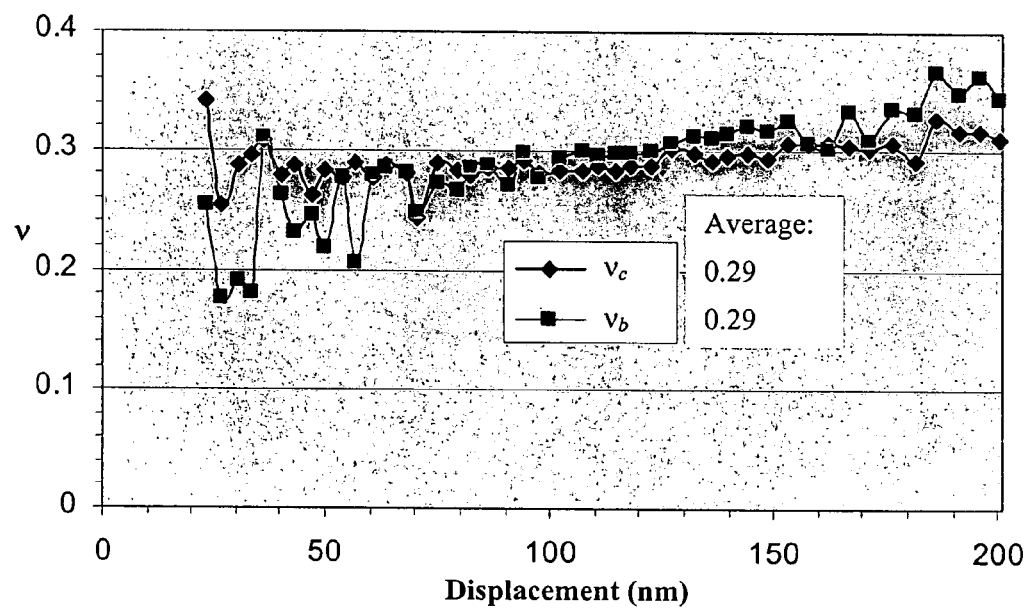
Figure 11A:
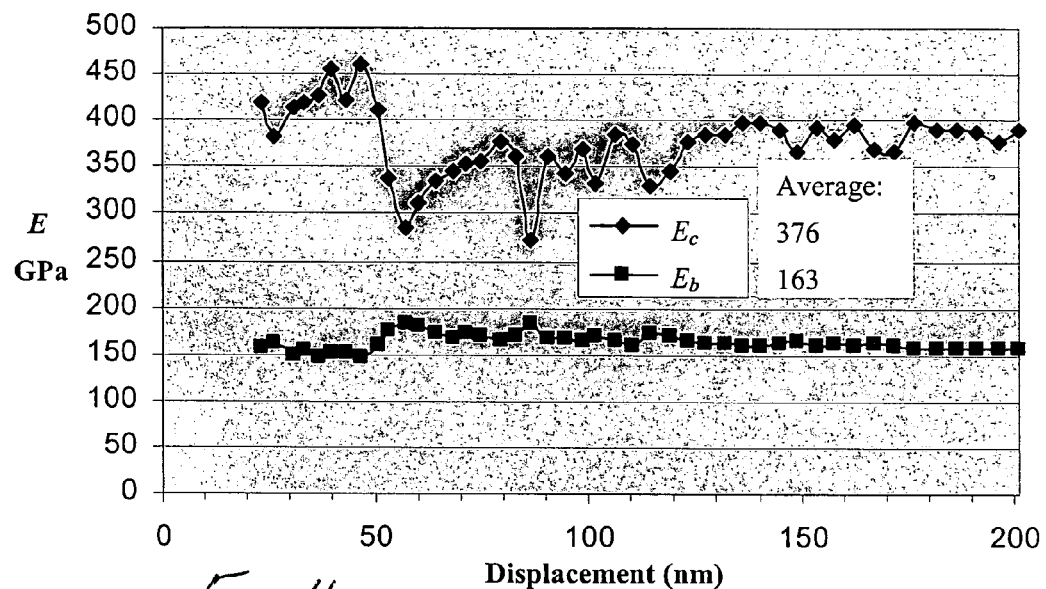
FIGS. 11a and 11b show predicted Young's modulus values and Poisson ratio values, respectively, for sample A2 for each discrete indentation measurement
Figure 11B:
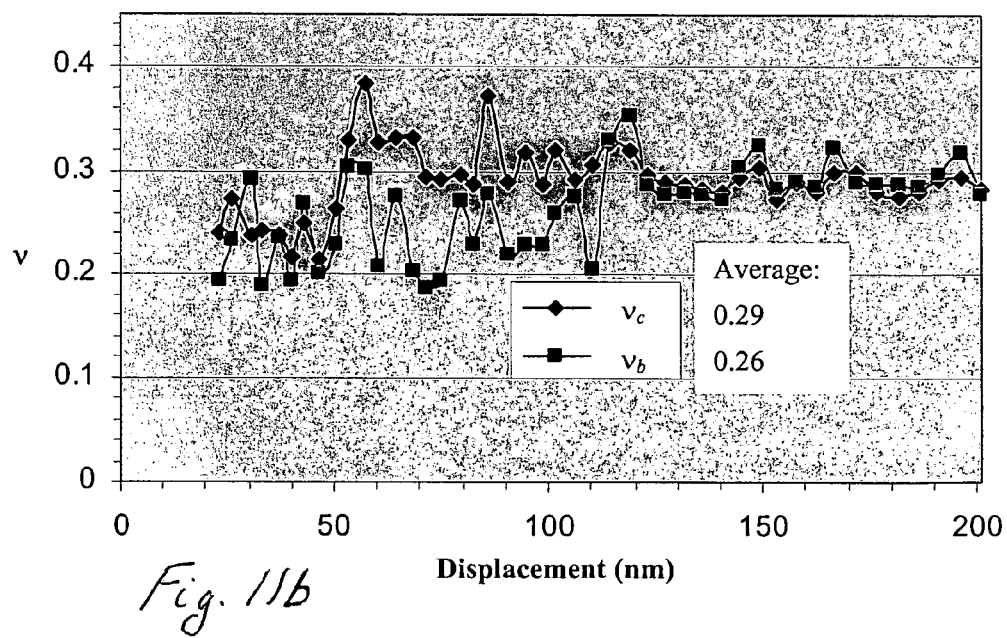
Figure 12A:
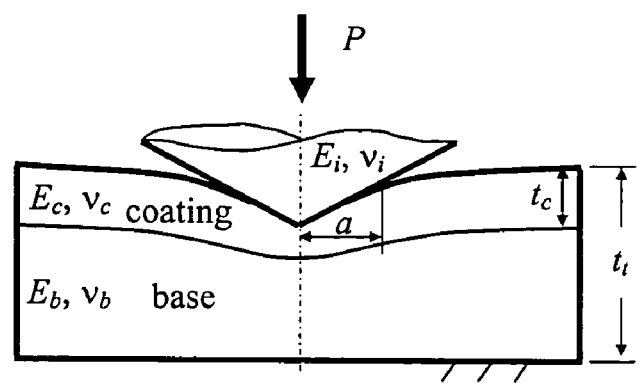
FIG. 12a shows a generic indentation test using a non-spherical tip.
Figure 12B:
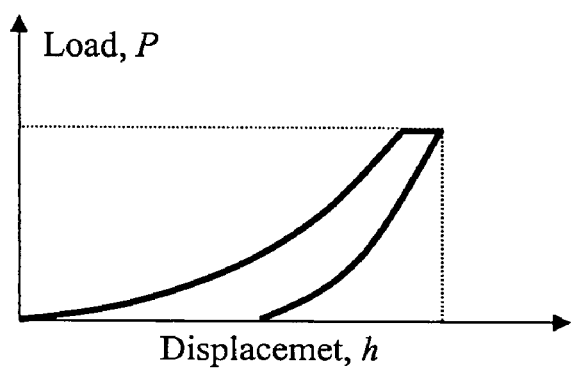
FIG. 12b shows a corresponding loading-unloading curve, where the elastic loading may be only a small portion and plastic deformation is unavoidable before the elastic unloading.

Two samples were prepared to demonstrate practice of embodiments of the invention. Commercial silicon wafers were the substrates on which TiN was deposited with two different thickness. A ball with a radius of 20 mm (FIG. 7c) was used to wear away the coatings and part of the substrate. Wear scars shown in FIGS. 7(a) and (b) were used to determine the coating thickness. Sample A1 and A2 have 2.08 and 3.15 micron thick coatings, respectively. Both samples have very smooth surfaces (Rq is around 10 nm) except some scattering particles (see FIG. 7 around the wear scars). Load and displacement curves were obtained by using a commercial nano-indentation system and a sapphire sphere with the following parameters: Young's modulus of 441 GPa, Poisson's ratio of 0.234, and radius of 122 microns ($E^*_i$=466.55 GPa). Nine tests are carried out and average indentation data were shown in FIG. 8 with error bar standing for the standard deviation. For the silicon wafers, Poisson's ratio is assumed as 0.27 (Reference: Chudoba et al. 2000) and Young's modulus is measured to be around 159 GPa ($E^*_b$=171.50 GPa). By using these properties, coating thickness, and Eqs. (1) and (2), FIG. 8 is transformed into FIG. 9 in a form of modified Young's modulus of samples vs normalized coating thickness. It is noted that two samples have very similar behavior as expected when $T_c$ is less than 1, corresponding to displacement for A1 greater than 23 nm. Although A1 has significant larger $E^*_s$ than A2 at $T_c>1$, the discrepancy is probably due to several uncertainties, such as roughness and shape of indenter tip. Material properties ($E_c$, $v_c$, $E_b$, $v_b$) of sample A1 and A2 are obtained by minimizing Eq. (12) with all indentation data from 23 to 200 nm displacement and are shown in FIG. 10a and 10b and 11a and 11b, respectively. The average Young's modulus for each TiN coating is 383 or 376 GPa, which agree with each other well and are close to the measurements obtained by Reference: Schneider and Tucker (1996). The average Poisson's ratio for each TiN coating is 0.29. Also, the average Young's moduli of two silicon substrates measured for two samples are very close: 159 and 163 GPa, respectively.

The invention is not limited to practice using the particular substrates and coatings and indenters described in the above examples and can be practiced with a wide variety of substrates having a wide variety of coatings thereon using different indenters to determine mechanical properties thereof as described.

Indentation Data Probed by Other Types of Indenters

Pursuant to another embodiment of the invention, Equation 8 [Eq. (8)] is applicable in the elastic regime for other types of indenters, beside the spherical shape. The parameters α in Eq. (8) is expected to be a function of non-dimensional coating thickness and depends on the indenter shape. Note that the coating thickness is normalized by characteristic length determined from projected area (A) of contact between the indenter and the sample: $T_c = t_c \sqrt{\pi/A}$. With a given indenter shape, α values could be determined beforehand with the same procedure described above. In order to be simple, the α values for spherical indenters could be adopted here approximately. For sharp indenters, the uncertainty in the elastic loading portion may be high due to the limit of the instruments. Data in the elastic unloading portion could be used in our approaches with appropriate consideration of the impression due to plastic deformation. Similar to the procedure for the spherical indenter, the procedure used to determine Young's modulus and Poisson's ratio of the coating and the substrates from the indentation data probed by any indenters is described as follows:

1. The sample is prepared and the indenter instrument properly calibrated.
2. The coating thickness of the sample is known or measured with proper methods. Choose an indenter made of diamond, sapphire, ruby, tungsten carbide, or other materials.
3. Record the modified Young's modulus of the indenter, if it is available.
4. A calibration sample with known material properties, e.g. fused silica, can be used to calibrate the area function of the indenter. After the calibration sample is indented by the indenter, the load-displacement curve is obtained. Conventional methods are used to find the area function.
5. Record one or several curves of the load and the displacement.
6. Use conventional methods to obtain A and $E_{i,s}$ with load and displacement values corresponding to measured data points in the unloading portion.
7. $T_c$ is evaluated by $T_c = t_c \sqrt{\pi/A}$.
8. Use Eq. (2) to find $E^*_s$.
9. Equation (8) is used to find $E_c$ and $v_c$, and to find $E_b$ and $v_b$ as well if they are unknown. Conventional minimization analysis can be used to find values of these properties by minimizing (i.e. minimizing error) the following expression rewritten from Eq. (8), $$\left| E^*_s - E^*_c \frac{1 - (\lambda + \kappa + 4\kappa\alpha^2)\theta + \lambda\kappa\theta^2}{1 + 4\alpha\kappa\theta - \lambda\kappa\theta^2} \right| \quad (12)$$

Although the invention has been described in connection with certain embodiments thereof, those skilled in the art will appreciate that the invention is not so limited and that changes, modifications, and the like can be made thereto within the scope of the invention as set forth in the appended claims.

REFERENCES

Bhushan, B, *Handbook of Micro/Nano Tribology*, 1999, CRC Press.

Fischer-Cripps, A., *Nanoindentation*, 2002, Springer.

Schneider, D., Schwaz, T., and Schultrich, B., 1992, "Determination of Elastic Modulus and Thickness of Surface Layers by Ultrasonic Surface Waves," *Thin Solid Films*, Vol. 219, n1–2, pp 92–102.

Fang, W., 1999, "Determination of the Elastic Modulus of Thin Film Materials Using Self-Deformed Micromachined Cantilevers," *Journal of Micromechanics and Microengineering*, Vol. 9, n3, pp 230–235.

Loubet, J. L., Georges, J. M., Marchesini, O., and Meille, G., 1984, "Vickers Indentation Curves of Magnesium Oxide (MgO)," Journal of Tribology, Vol. 106, pp. 43–48.

Doerner, M. F. and Nix, W. D., 1986, "A Method for Interpreting the Data from Depth-Sensing Indentation Instruments," Journal of Materials Research, Vol. 1, no. 4, pp. 601–609.

Pharr, G. M., Oliver, W. C., Brotzen, F. R., 1992, "On the Generality of the Ralationship among Contact Stiffness, Contact Area, and Elastic Modulus During Indentation," Journal of Materials Research, Vol. 7, no. 3, pp. 613–617.

Oliver, W. C. and Pharr, G. M., 1992, "An Improved Technique for Determining Hardness and Elastic Modulus Using Load and Displacement Sensing Indentation Experiments," Journal of Materials Research, Vol. 7, no. 6, pp. 1564–1583.

Chudoba, T., Schwarzer, N., and Richter, F., 2002, "Steps towards a mechanical modeling of layered systems," Surface and Coatings Technology, 154 (2–3), pp. 140–151.

Gao, H. J., Chiu, C. H., and Lee, J., 1992, "Elastic Contact Versus Indentation Modeling of Multilayered Materials," International Journal of Solids and Structures, 29 (20), pp. 2471–2492.

Menčik, J., Munz, D., Quandt, E., Weppelmann, E. R., and Swain, M. V., 1997, "Determination of Elastic Modulus of Thin Layers Using Nanoindentation," Journal of Materials Research, Vol. 12, no. 9, pp 2475–2484.

Lim, Y. Y., Chaudhri, M. M., and Enomoto, Y., 1999, "Accurate Determination of the Mechanical Properties of Thin Aluminum Films Deposited on Sapphire Flats using Nanoindentations," *Journal of materials research, Vol.* 14 (6), pp 2314–2326.

Wallace, J. S. and Ilavsky, J., 1998, "Elastic Modulus Measurements in Plasma Sprayed Deposits," Journal of Thermal Spray Technology, Vol. 7 (4), pp 521–526.

Herbert, E. G., Pharr, G. M., Oliver, W. C., Lucas, B. N., Hay, J. L., 2001, "On the Measurement of Stress-strain Curves by Spherical Indentation," *Thin Solid Films*, Vol. 398–399, pp 331–335.

Chudoba, T., Schwarzer, N., and Richter, F., 2000, "Determination of elastic properties of thin films by indentation measurements with a spherical indenter," Surface and Coatings Technology, 127 (1), pp 9–17.

Hertz, H., 1882, "Über die Berührung fester elastischer Körper" (on the contact of elastic solids), J. reine und angewandte Mathematik, Vol. 92, pp 156–171.

Johnson, K. L., 1985, Contact Mechanics, Cambridge University Press.

Liu, S. B. and Wang, Q., 2000, "A Three-Dimensional Thermomechanical Model of Contact Between Non-Conforming Rough Surfaces," Journal of Tribology, Vol. 123, pp 17–26.

Schneider, D. and Tucker, M. D., 1996, "Non-destructive Characterization and Evaluation of Thin Films by Laser-induced Ultrasonic Surface Waves," Thin Solid Films, 290–291, pp 305–311.

Nogi, T. and Kato, T. 1997, "Influence of a Hard Surface Layer on the Limit of Elastic Contact-Part 1: Analysis Using a Real Surface Model", ASME Journal of Tribology, 119, pp. 493–500.

What is claimed is:

1. A method of determining Young's modulus of a coating on a substrate comprising a coated sample, comprising the steps of generating load versus displacement indentation data using an indenter to indent the coated sample in an elastic range of the coating; determining a modified Young's modulus of the coated sample ($E^*_s$) using the indentation data; and determining the Young's modulus of the coating ($E_c$) using a relationship that expresses the modified Young's modulus of the coated sample ($E^*_s$) as a function of Young's modulus and Poisson's ratio of the coating, Young's modulus and Poisson's ratio of the substrate, and a parameter related to thickness of the coating.

2. The method of claim 1 wherein the relationship is expressed as:

$$E^*_s = E^*_c \frac{1 - (\lambda + \kappa + 4\kappa\alpha^2)\theta + \lambda\kappa\theta^2}{1 + 4\alpha\kappa\theta - \lambda\kappa\theta^2} \quad (8)$$

where $$\tau = \frac{E_c(1+v_b)}{E_b(1+v_c)}$$

is the shear modulus ratio;

$$\kappa = \frac{\tau - 1}{\tau + (3 - 4v_c)} \quad \text{and} \quad \lambda = 1 - \frac{4(1-v_c)}{1 + \tau(3-4v_c)},$$

and $\theta = \exp(-2\alpha)$ where parameter $\alpha$ is related to non-dimensional coating thickness.

3. The method of claim 1 further including determining the Poisson's ratio of the coating using the relationship.

4. The method of claim 1 further including determining Young's modulus of the substrate using the relationship.

5. The method of claim 1 further including determining Poisson's ratio of the substrate using the relationship.

6. The method of claim 1 wherein the indentation data is generated using the indenter having at least a partial spherical surface.

7. The method of claim 6 wherein the partial spherical surface has a radius greater than the thickness of the coating.

8. The method of claim 1 wherein the indenter includes an uncoated surface.

9. The method of claim 1 wherein the indenter includes a coated surface.

10. In a method of determining Young's modulus of a coating on a substrate, the improvement comprising using the following relationship in determination of the Young's modulus:

$$E^*_s = E^*_c \frac{1 - (\lambda + \kappa + 4\kappa\alpha^2)\theta + \lambda\kappa\theta^2}{1 + 4\alpha\kappa\theta - \lambda\kappa\theta^2} \quad (8)$$

where $$\tau = \frac{E_c(1+v_b)}{E_b(1+v_c)}$$

is the shear modulus ratio;

$$\kappa = \frac{\tau - 1}{\tau + (3 - 4v_c)} \quad \text{and} \quad \lambda = 1 - \frac{4(1-v_c)}{1 + \tau(3-4v_c)},$$

and $\theta = \exp(-2\alpha)$ where parameter $\alpha$ is related to non-dimensional coating thickness, said relationship expressing the measured modified Young's modulus of the coated substrate ($E^*_s$) as a function of Young's modulus and Poisson's ratio of the coating, Young's modulus and Poisson's ratio of the substrate, and parameter $\alpha$.

11. The method of claim 10 wherein parameter a is related to non-dimensional coating thickness $T_c$ where $T_c = t_c/\alpha_0$ and $t_c$ is measured coating thickness and $\alpha 0$ is contact radius of the indentation, said parameter a being determined by using indentation displacement data and Equation (10).

12. In a method of determining Young's modulus of a coating on a substrate comprising a coated sample, the improvement comprising the steps of generating load versus displacement indentation data using an indenter to indent the coated sample in an elastic range of the coating; determining a modified Young's modulus of the coated sample ($E^*_s$) that is dependent on coating thickness using the indentation data; and determining the Young's modulus of the coating itself using the modified Young's modulus of the coated sample ($E^*_s$).

13. The method of claim 12 wherein the indenter has at least a partial spherical surface.

14. The method of claim 13 wherein the partial spherical surface has a radius greater than the thickness of the coating.

15. The method of claim 12 wherein the indenter includes an uncoated surface.

16. The method of claim 12 wherein the indenter includes a coated surface.

17. The method of claim 12 wherein the modified Young's modulus of the coated sample ($E^*_s$) is a function of dimensionless coating thickness.

* * * * *

UNITED STATES PATENT AND TRADEMARK OFFICE
CERTIFICATE OF CORRECTION

PATENT NO. : 7,165,463 B2 Page 1 of 1
APPLICATION NO. : 10/964589
DATED : January 23, 2007
INVENTOR(S) : Shuangbiao Liu et al.

It is certified that error appears in the above-identified patent and that said Letters Patent is hereby corrected as shown below:

Claim 11 line 38: replace "a" with --$\alpha$--
Claim 11 line 40: replace "$\alpha 0$" with --$\alpha_0$--
Claim 11 line 41: replace "a" with --$\alpha$--

Signed and Sealed this

First Day of April, 2008

JON W. DUDAS
*Director of the United States Patent and Trademark Office*

UNITED STATES PATENT AND TRADEMARK OFFICE
CERTIFICATE OF CORRECTION

PATENT NO.       : 7,165,463 B2                                     Page 1 of 1
APPLICATION NO.  : 10/964589
DATED            : January 23, 2007
INVENTOR(S)      : Shuangbiao Liu et al.

It is certified that error appears in the above-identified patent and that said Letters Patent is hereby corrected as shown below:

<u>Column 14</u>
    Claim 11 line 38: replace "a" with --$\alpha$--
    Claim 11 line 40: replace "$\alpha 0$" with --$\alpha_0$--
    Claim 11 line 41: replace "a" with --$\alpha$--

This certificate supersedes the Certificate of Correction issued April 1, 2008.

Signed and Sealed this

Sixth Day of May, 2008

JON W. DUDAS
*Director of the United States Patent and Trademark Office*